(12) United States Patent
Makkad et al.

(10) Patent No.: US 11,427,661 B2
(45) Date of Patent: Aug. 30, 2022

(54) FLUORESCENT POLYMER FOR VISUAL SOLID AND AQUEOUS STATE SENSING OF VOLATILE ORGANIC COMPOUNDS

(71) Applicant: COUNCIL OF SCIENTIFIC AND INDUSTRIAL RESEARCH, New Delhi (IN)

(72) Inventors: Sarabjot Kaur Makkad, Maharashtra (IN); Asha Syamakumari, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 16/971,438

(22) PCT Filed: Feb. 18, 2019

(86) PCT No.: PCT/IN2019/050129
§ 371 (c)(1),
(2) Date: Aug. 20, 2020

(87) PCT Pub. No.: WO2019/162960
PCT Pub. Date: Aug. 29, 2019

(65) Prior Publication Data
US 2021/0088449 A1    Mar. 25, 2021

(30) Foreign Application Priority Data

Feb. 22, 2018    (IN) .............................. 201811006753

(51) Int. Cl.
| | | |
|---|---|---|
| *C08F 112/08* | (2006.01) | |
| *G01N 21/77* | (2006.01) | |
| *C09B 69/10* | (2006.01) | |
| *G01N 31/22* | (2006.01) | |
| *G01N 33/22* | (2006.01) | |

(Continued)

(52) U.S. Cl.
CPC .......... *C08F 112/08* (2013.01); *C09B 69/102* (2013.01); *G01N 21/6428* (2013.01); *G01N 21/77* (2013.01); *G01N 31/223* (2013.01); *G01N 33/0036* (2013.01); *G01N 33/22* (2013.01);

(Continued)

(58) Field of Classification Search
CPC .... C08F 112/08; C08F 212/08; C09B 69/102; G01N 21/6428; G01N 21/77; G01N 31/223; G01N 33/0036; G01N 33/22; G01N 33/587; G01N 2021/7786
See application file for complete search history.

(56) References Cited

U.S. PATENT DOCUMENTS

| | | | |
|---|---|---|---|
| 9,631,066 B2 | 4/2017 | Syamakumari et al. | |
| 2006/0153924 A1* | 7/2006 | Griffiths ............. | G01N 21/6428 424/490 |
| 2015/0183956 A1* | 7/2015 | Syamakumari ...... | C08K 5/3437 525/282 |

OTHER PUBLICATIONS

Musyanovych et al., "Grafting of Amino Functional Monomer onto Initiator-Modified Polystyrene Particles", 2005, Langmuir, 21,6,2209-2217 (Year: 2005).*

(Continued)

*Primary Examiner* — Samuel P Siefke
*Assistant Examiner* — Henry H Nguyen

(57) ABSTRACT

The present invention provides a fluorescent polymer comprising a fluorophore perylene bisimide (PBI) and oligo (p-phenylene vinylene) (OPV) functionalized with carboxy and amine functionality groups and a polystyrene (PS) backbone for the detection of volatile organic compound, a process for the detection and a kit thereof.

5 Claims, 4 Drawing Sheets

(51) Int. Cl.
   *G01N 33/00*   (2006.01)
   *G01N 21/64*   (2006.01)
   *G01N 33/58*   (2006.01)
   *C08F 212/08*  (2006.01)

(52) U.S. Cl.
   CPC .......... *G01N 33/587* (2013.01); *C08F 212/08* (2013.01); *G01N 2021/7786* (2013.01)

(56) References Cited

OTHER PUBLICATIONS

Sonawane et al., "Fluorescent Cross-Linked Polystyrene Perylenebisimide/Oligo(p-Phenylenevinylene) Microbeads with Controlled Particle Size, Tunable Colors, and High Solid State Emission" ACS Applied Materials & Interfaces, vol. 5, 2013, pp. 12205-12214.

Makkad et al., "π-Conjugated Chromophore Incorporated Polystyrene Nanobeads as Single Optical Agent for Three-Channel Fluorescent Probe in Bioimaging Application" ACS Biomaterials Science & Engineering, vol. 3, 2017, pp. 1788-1798.

Tan et al., "PMMA Microspheres with Embedded Lanthanide Nanoparticles by Photoinitiated Dispersion Polymerization with a Carboxy-Functional Macro-RAFT Agent" Macromolecules, vol. 48, 2015, pp. 3629-3640.

Pang et al.,"A Rare L1D + R1D — 3D Luminescent Dense Polymer as Multifunctional Sensor to Nitro Aromatic Compounds, Cu2+, and Bases" Crystal Growth & Design, vol. 14, 2014, pp. 2954-2961.

Yang et al., "Highly Selective Bifunctional Luminescent Sensor toward Nitrobenzene and Cu2+ Ion Based on Microporous Metal-Organic Frameworks: Synthesis, Structures, and Properties" ACS Applied Materials & Interfaces, vol. 9, 2017, pp. 17208-17217.

Huang et al., "A Luminescent Metal-Organic Framework for Highly Selective Sensing of Nitrobenzene and Aniline" RSC Advances, Journal Name, 2016, 4 pages, [Published on Sep. 6, 2016; Downloaded by Cornell University Library on Jul. 9, 2016 05:02:00].

Cao et al., "Selective Sensing of Fe3+ and Al3+ Ions and Detection of 2,4,6-Trinitrophenol by a Water-Stable Terbium-Based Metal-Organic Framework" Chemistry a European Journal, vol. 21, 2015, pp. 15705-15712.

Holzapfel et al., "Preparation of Fluorescent Carboxyl and Amino Functionalized Polystyrene Particles by Miniemulsion Polymerization as Markers for Cells" Macromolecular Chemistry and Physics, vol. 206, 2005, pp. 2440-2449.

Sandeep et al., "Supercoiled fibres of self-sorted donor-acceptor stacks: a turn-off/turn-on platform for sensing volatile aromatic compounds" Chemical Science, vol. 7, 2016, pp. 4460-4467.

* cited by examiner

FLUORESCENT POLYMER FOR VISUAL SOLID AND AQUEOUS STATE SENSING OF VOLATILE ORGANIC COMPOUNDS

CROSS REFERENCE TO RELATED APPLICATIONS

This application is a National Stage of International Application No. PCT/IN2019/050129, filed on Feb. 18, 2019, which claims priority to Indian Patent Application No. 201811006753, filed on Feb. 22, 2018, the disclosures of which are incorporated by reference in their entirety.

FIELD OF THE INVENTION

The present invention relates to a fluorescent polymer for visual solid and liquid state sensing of volatile organic compounds or analyte. More particularly, the present invention relates to a fluorescent polymer comprising a fluorophore perylene bisimide (PBI) and oligo (p-phenylene vinylene) (OPV) functionalized with carboxy and amine functionality groups and a polystyrene (PS) backbone for the detection of volatile organic compound, a process for the detection and a kit thereof.

BACKGROUND AND PRIOR ART OF THE INVENTION

The need to continuously monitor and quantify an analyte (volatile organic compounds) or an environmental parameter in the fastest and cheapest way has been the driving force of sensor research for several decades. Given its facile operation, remote monitoring, easy read-out and high sensitivity, fluorescence is by far the most applied detection method. The solid-state luminescent materials (organic, inorganic, and polymers) have tremendous demand in the field of material science due to their high impact in applications like solid state light emitters, bio and chemosensor, security and color tuning material for optical recording etc. The functional materials including $\pi$-conjugated electron-rich small molecules, polyelectrolyte, quantum dots, microporous metal-organic frameworks (MOFs), polyrotaxane coordination polymers, conjugated polymers based on polyfluorenes, poly-(phenylenevinylene)s (PPV) and oligo (phenylenevinylene) (OPV), molecularly imprinted polymers (MIPs), etc., have been developed as high-performance fluorescence sensing materials. Although these are promising materials, the effort involved in their synthesis makes them less favorable.

The fluorescent polymeric microspheres with controlled particle size, high photostability, tunable emission properties, and thermal stability make them suitable as micro- or nanosensors for analysis and device fabrication. For instance, M. A. Winnik et al. reported lanthanide metal-encoded polystyrene microbeads where the postfunctionalization of fluorescent microbeads with analyte was applied for highly multiplexed bioassay (*Macromolecules*, 2015, 48 (11), pp 3629-3640). Fluorescent microbeads are usually synthesized by physical entrapment of dye in a polymer matrix such as poly(methyl methacrylate), polysilane, poly-vinyl chloride, polystyrene, and cellulose acetate.

U.S. Pat. No. 9,631,066 disclosed a composition comprising a fluorescent chromophore as cross linker incorporated to polymer beads, wherein the fluorescence of the composition occurs in solid state and solution state with high quantum yield in solid state. The fluorescent cross-linked polymer comprising a fluorescent chromophore as a cross linker incorporated into a polymer, wherein the composition exhibits fluorescence in solid state and solution state, having quantum yield in the range of (Powder) 0.25% to 0.71%. The composition is prepared by two stage dispersion polymerization in ethanol.

Article titled "n-Conjugated chromophore incorporated polystyrene nanobeads as single optical agent for three-channel fluorescent probe in bioimaging application" by S K Makkad et al. published in *ACS Biomater. Sci. Eng.*, 2017, 3 (8), pp 1788-1798 reports Fluorescent polystyrene (PS) nanobeads in the size range ~70-120 nm incorporating perylene bisimide (PBI-PS) and/or oligo(p-phenylenevinylene) (OPV-PS) developed by miniemulsion polymerization technique. A dye loading content (DLC) of <3% was sufficient to impart high fluorescence emission capability to the PS beads.

Although dual sensors have been reported, their response towards the different class of analytes are usually similar—through the attenuation in their emission intensity; i.e. emission quenching of sensing material in all cases. For instance, Wang et al (*Cryst. Growth Des.* 2014, 14, 2954-296) reported dual sensing of Nitroaromatic compounds and copper ion; Zang et al (*Chem. Eur. J.* 2015, 21, 15705-15712) reported detection of explosives and multiple cations in water, Yang et al (*ACS Appl. Mater. Interfaces* 2017, 9, 17208-17217) reported detection of nitrobenzene and copper ion while the report from the group of Han et. al (*RSC Adv.*, 2016, 6, 87945-87949) explored dual sensing of nitrobenzene and aniline through fluorescence quenching.

A different class of 'supramolecular stack' of sensor was reported from the group of Ajayaghosh et. al (*Chem. Sci.*, 2016, 7, 4460-4467) where two active sensors based on oligophenylene vinylene (OPV) and perylene bisimide (PBI) were physically mixed to form self assembled stacks that was responsive towards both nitroorganics as well as nitroamine. Unlike sensors based on physical mixtures of small fluorescent molecules a robust polymer based sensor is amenable to large scale application since it has the scope of casting into free standing films (which is an important prerequisite for on-field use in devices) or enhancing the sensing efficiency by its surface modification.

Therefore, there is need for polymer based "dual-distinct" solid state sensor. Accordingly, the present invention provides a fluorescent polymer comprising a fluorophore with carboxy and amine functionality groups and a polystyrene (PS) backbone for effective sensing of volatile organic compounds.

OBJECTIVES OF THE INVENTION

The main objective of the present invention is to provide a fluorescent polymer comprising a fluorophore perylene bisimide (PBI) and oligo (p-phenylene vinylene) (OPV) functionalized with carboxy and amine functionality groups and a polystyrene (PS) backbone.

Another objective of the present invention is to provide a process for the detection of volatile organic compounds or analytes selected from electron rich or electron deficient moieties using a fluorescent polymer comprising a fluorophore perylene bisimide (PBI) and oligo (p-phenylene vinylene) (OPV) functionalized with carboxy and amine functionality groups and a polystyrene (PS) backbone.

Still another objective of the present invention is to provide amine functionalized OPV incorporated PS nanobeads for sensing nitro-explosives such as picric acid in water.

Yet another objective of the present invention is to provide a kit for the detection of visual solid and liquid state sensing volatile organic compounds comprising the fluorescent polymer having both perylene bisimide (PBI) and oligo (p-phenylene vinylene) (OPV) fluorophores with carboxy and amine functionality.

SUMMARY OF THE INVENTION

Accordingly, the present invention provides a fluorescent polymer comprising a fluorophore perylene bisimide (PBI) and oligo (p-phenylene vinylene) (OPV) functionalized with carboxy and amine functionality groups and a polystyrene (PS) backbone.

In preferred embodiment, the fluorescent polymer is in the form of nanobeads. The size of the polystyrene nanobeads is in the range of 70 to 180 nm.

In an embodiment, the present invention provides a process for the detection of analytes using fluorescent polymer having both perylene bisimide (PBI) and oligo (p-phenylene vinylene) (OPV) fluorophores with carboxy and amine functionality comprises exposing the polymer directly to the analyte.

In another embodiment, the present invention provides a dual vapour based solid and liquid state emitting sensor having donor and acceptor dyes together into polystyrene nanobeads.

In still another embodiment, the present invention provides a kit for the detection of volatile organic compounds comprising fluorescent polymer having both perylene bisimide (PBI) and oligo (p-phenylene vinylene) (OPV) fluorophores with carboxy and amine functionality.

In yet another embodiment, the present invention provides sensor for sensing explosives in water.

DETAILED DESCRIPTION OF THE INVENTION

Figure 1:
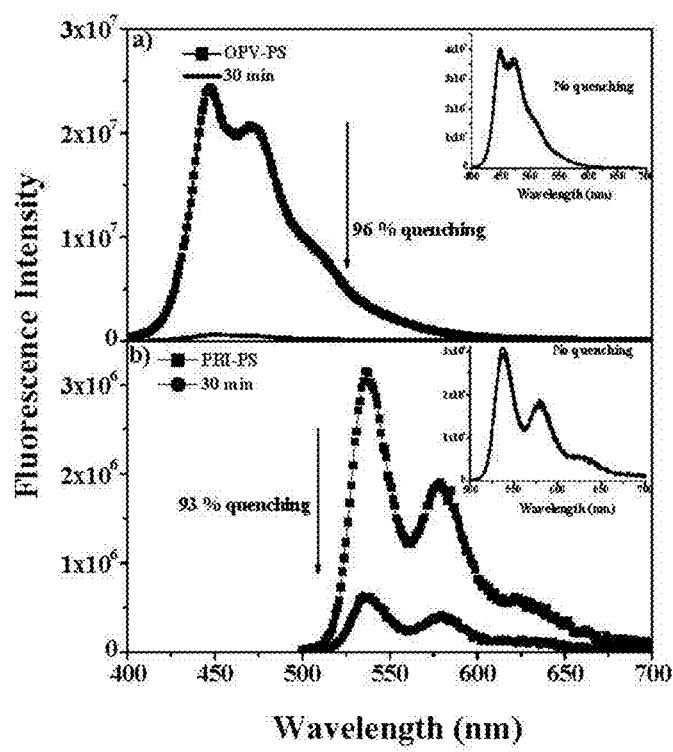
FIG. 1: Solid state emission and excitation spectra of the polymers. (a) Quenching of OPV emission upon exposure to nitrobenzene vapor (Inset: OPV emission remain unquenched after exposure to o-toulidine vapor). (b) Quenching of PBI emission upon exposure to o-toulidine vapors. (Inset: PBI emission remain unquenched after exposure to nitrobenzene vapor).

The invention will now be described in detail in connection with certain preferred and optional embodiments, so that various aspects thereof may be more fully understood and appreciated.

The term "analyte" and "volatile organic compounds" are used alternatively in the specification; however both have the same meaning. Visual means detection by naked eye.

In view of the above, the present invention provides a fluorescent polymer comprising a fluorophore perylene bisimide (PBI) and oligo (p-phenylene vinylene) (OPV) functionalized with carboxy and amine functionality groups and a polystyrene (PS) backbone and a process for the preparation thereof. The fluorophores are incorporated into the polystyrene nanobeads in a fashion to have near white emission under UV light.

The conjugated dyes in the form of oligo(p-phenylene vinylene) (OPV) and perylene bisimide (PBI) based crosslinkers are synthesized. These dyes are used for miniemulsion co-polymerization with other monomers including styrene and functional monomers. Use of potassium persulfate as initiator and Sodium Dodecyl Sulphate (SDS) (surfactant) without any functional monomer for the miniemulsion polymerization resulted in the formation of non-functionalized polystyrene nanobeads, PS-KPS.

The functional monomer is selected from acrylic acid (AA) or aminoethyl methacrylate hydrochloride (AEMH). In the synthesis of functionalized polystyrene nanobeads, acrylic acid (AA) or aminoethyl methacrylate hydrochloride (AEMH) is used as functional monomer to cause the presence of required functionality in PS—COOH and PS-NH$_2$ respectively.

The surface charge of the polystyrene nanoparticles observed from zeta potential measurement at pH=7 using KCl as background electrolyte is used to interpret the different functionalities on the nanoparticles. PS—COOH shows a net negative zeta potential of –38 mV, indicating the presence of carboxy functionality on the surface of the nanoparticles, along with few sulfate groups from surfactant. Further confirmation for presence of functional groups is observed from FTIR spectroscopic analyses which clearly showed characteristic peaks for respective functional groups. For PS—COOH, broad peak at 3444-2500 cm$^{-1}$ accounted for combination of carboxylic O—H and C—H stretching. Peak at 1709 cm$^{-1}$ corresponded to C=O stretching of acid while peak at 1204 cm$^{-1}$ and 971 cm$^{-1}$ corresponded to C—O and O—H bending of the acid functionality. For PS-NH$_2$, characteristic peak for N—H stretching and bending (in-plane) appeared at 3425 cm$^{-1}$ and 1604 cm$^{-1}$ respectively while broad peak corresponding to C—N stretching appeared at 1129 cm$^{-1}$. It is important to note that none of the characteristic peaks for —COOH or —NH$_2$ functionality was observed in the case of PS-KPS.

The polymers of the present invention are found to possess high molecular weight in the range of 114600 to 157600 with a Polydispersity Index (PDI) varied from 2.3 to 3.1. The observed values for molecular weight tabulated in Table 1 and their corresponding GPC chromatogram showed good consistency for the tested samples. The polystyrene nanobeads are observed to have a uniform profile for size distribution. DLS particle size analysis showed that effective diameter of the synthesized nanoparticles are comparable for all the cases (Table 1), with an average value of 72 nm for PS—COOH, 129 nm for PS-KPS and 184 nm for PS-NH$_2$.

Absorption spectra of the polymers from tetrahydrofuran (THF) solution showed the presence of two characteristic peaks corresponding to both the fluorophore crosslinkers, i.e. OPV and PBI. A comparative study with the individual absorption peaks for all the three nanobeads (namely PS-NH$_2$, PS—COOH, PS-KPS) with that of pristine crosslinkers revealed a blue shift by 30 nm for absorption maxima of OPV, while absorption maxima of PBI remained unaffected.

A comprehensive detail of DLC and DLE values for all the polymers has been presented in Table 1.

TABLE 1

Sample designation, Dye Loading Content (DLC), Dye Loading Efficiency (DLE), Polydispersity Index (Đ).

| Samples | PS-KPS | PS-COOH | PS-NH2 |
|---|---|---|---|
| Mn | 157600 | 122200 | 114600 |
| Mw | 464500 | 379900 | 264090 |
| PDI | 2.9 | 3.1 | 2.3 |
| Solid Content (%) | 14 | 15.8 | 13.4 |
| Zeta Potential (mV) | −19 | −38 | +39 |
| Particle Size (nm) | 129 | 72 | 184 |
| PDI | 0.07 | 0.12 | 0.09 |
| Amount of OPV in feed (actual incorporation) (mg/g of styrene) | 0.7 (0.18) | 0.7 (0.16) | 0.7 (0.40) |
| Amount of PBI in feed (actual incorporation) (mg/g of styrene) | 2 (0.53) | 2 (0.42) | 2 (0.30) |
| DLC (%) OPV (PBI) | 0.02 (0.05) | 0.02 (0.04) | 0.04 (0.03) |
| DLE (%) OPV (PBI) | 26 (26.5) | 23 (21) | 57 (15) |
| Solid State Quantum Yield (%) OPV (PBI) | 26 (42) | 32 (65) | 39 (78) |

Similarly the characterization details for the PS with OPV alone is given below.

The OPV dye is covalently incorporated into polystyrene backbone through miniemulsion co-polymerization, using non-ionic Brij S-100 as surfactant and 4,4'-Azobis(4-cyanovaleric acid) (ACVA) as initiator. Aminoethyl methacrylate hydrochloride (AEMH) is used as functional monomer to functionalize the surface of the resulting nanobeads (PS—OPV-NH$_2$) with —NH$_2$ group, creating favourable sites for interaction with electron deficient compounds as incoming analyte. The surface charge is confirmed by a net elevated positive zeta potential of +36.6 mV, indicating presence of —NH$_2$ groups on the surface (Table 2).

TABLE 2

Number and weight average molar mass, polydispersity indices (PDI), solid content, zeta potential of PS-OPV-NH$_2$.

| Sample | Mn[a] | Mw[a] | PDI[a] (Đ) | Solid content (%) | Zeta Potential[b] |
|---|---|---|---|---|---|
| PS-OPV-NH2 | 56700 | 151000 | 2.6 | 21 | 436.6 |

[a]Measured by Gel Permeation Chromatography (GPC) in Chloroform (CHCl$_3$) calibrated with linear, narrow molecular weight distribution polystyrene standards.
[b]Measured by Dynamic Light Scattering in water.

TABLE 3

Dye loading content (DLC), Dye loading efficiency (DLE), polydispersity index (D).

| Sample | Amount of OPV in feed (mg) | Amount of OPV incorporated (mg)a | DLC (%)[a] For OPV | DLE (%)[a] For OPV | Size (nm)[b] | PDI[b] |
|---|---|---|---|---|---|---|
| PS-OPV-NH2 | 30 | 16.1 | 1.6 | 53.6 | 182 | 0.08 |

[a]Dye Loading content (DLC) and Dye Loading Efficiency (DLE) are calculated by absorption studies in THF.
[b]Measured by Dynamic Light Scattering in water.

The solid state emission (collected at (a) 390 nm and (b) at 490 nm) as well excitation spectra were recorded for the polymers in powder form on a paper strip. Both the functionalized nanoparticles (PS—COOH and PS-NH$_2$) showed near-white emission under UV lamp while the non-functionalized PS-KPS nanoparticles show a light purple emission from their bulk phase powder. The emission spectra collected at 390 nm showed the characteristic emission peak for both OPV (390-500 nm) and PBI (500-700 nm) in all the polymers. Similar experimental condition was applied to measure the solid state quantum yield for each of the polymers, using integrating sphere attached with excitation source at 390 nm for OPV and 490 nm for PBI. The emission intensity of OPV from all the polymers showed a non linear trend, where PS-NH$_2$ having highest DLC (0.04%) measured the highest emission intensity. Although the DLC values were similar (0.02%) for the other two polymers, emission intensity for PS—COOH was found to be slightly higher as compared to PS-KPS. This trend of emission data was found to be consistent with the experimentally obtained quantum yield values, i.e highest for PS-NH$_2$ (39%) followed by PS—COOH (32%) and PS-KPS (29%).

In case of PBI, the emission intensity from the polymer followed a reverse trend, thus highest emission was observed for PS-NH$_2$, having lowest incorporation (DLC=0.030%) and PS—KPS having highest incorporation (DLC=0.053%) showed lowest emission. PS—COOH being moderately incorporated with PBI dye (DLC=0.042%), showed an intermediate emission under similar condition. Similar trend was also observed for solid state quantum yield values, i.e. highest for PS-NH$_2$ (78%), then PS—COOH (65%) and PS-KPS (42%).

The effective emission was minutely different for non-functionalized polymer (PS-KPS), showing light purple emission having CIE co-ordinate of (0.25, 0.21) while OPV-PS and PBI-PS polymers showcased blue and red emission respectively.

In one embodiment, the present invention provides PS nanobeads incorporating both OPV and PBI cross-linker together for sensing of both amines and nitroaromatics in vapour state.

In another embodiment, the present invention provides a process for the detection of analytes using fluorescent polymer having both perylene bisimide (PBI) and oligo (p-phenylene vinylene) (OPV) fluorophores with carboxy and amine functionality comprises exposing the polymer directly to the analyte.

In another embodiment, the present invention provides amine functionalized fluorescent OPV incorporated PS nanobeads are designed for sensing explosives in water.

The polymer is used in powder form or film form.

In a preferred embodiment, the process for the detection of analytes using fluorescent polymer having both perylene bisimide (PBI) and oligo (p-phenylene vinylene) (OPV) fluorophores with carboxy and amine functionality comprising the steps of:
a) securing transparent adhesive tape on a thin cardboard frame as a support followed by adhering polymer powder on said tape to obtain sample strip;
b) exposing said sample strip to the analyte vapour and performing photoluminescence (PL) measurement to check for sensing property;
c) preparing saturated vapour chambers by placing analytes inside a closed centrifuge tube for 24 to 30 hours at a temperature in the range of 25° C. to 30° C.;
d) placing the sample strips inside the centrifuge tube, avoiding any direct contact of the analyte with the sample and closing the chamber and
e) removing the sample from the vapour chamber and recording the emission spectra.

In another preferred embodiment, the process for the detection of analytes using fluorescent polymer having both perylene bisimide (PBI) and oligo (p-phenylene vinylene) (OPV) fluorophores with carboxy and amine functionality comprising the steps of.
a) pouring the solution of polymer in solvent into a petri dish and allowing the solvent to evaporate at a temperature in the range of 25° C. to 30° C. to afford film;
b) dipping the film of step (a) into alcoholic solution of the analyte and removing to soak off the excess liquid from the film surface to afford dried film;
c) recording the emission spectra with the dried film;
d) optionally dispersing the polymer in water preferably deionized water followed by adding analytes to form solution;
e) subjecting the through mixing of solution of step (d) followed by immediate recording of the emission spectra.

The alcoholic solution is selected from the group consisting of methanol, ethanol, propanol, isopropanol or butanol.

The invention provides a dual distinct sensor which will give distinct emission when come in contact with vapours of either amines or nitroaromatics. PS nanobeads are functionalized with amine and carboxy on the surface and comparative study is made on their ability to sense based on their functional group (PS-NH$_2$ (amine), PS—COOH (carboxy), PS-KPS (non-functionalized)). As the PS nanobeads contain both OPV and PBI in a single bead; OPV emission will quench when come in contact with nitroaromatics (OPV being a well-known donor) while PBI emission will quench on coming in contact with amines (PBI being an acceptor molecule). It would be turn off sensor if only one of the two (either OPV or PBI) would have been incorporated inside the polystyrene backbone as shown in FIG. 1 but by incorporating both the dyes together in the single nanobead imparted the sensor its "dual-distict" feature. The polymers beads are high molecular weight, free standing film can be made out of it. On dipping the film in either of analyte solution, one can get fast exchange of analyte and visual color change from blue to yellow and vice versa within 1 min.

Figure 2:
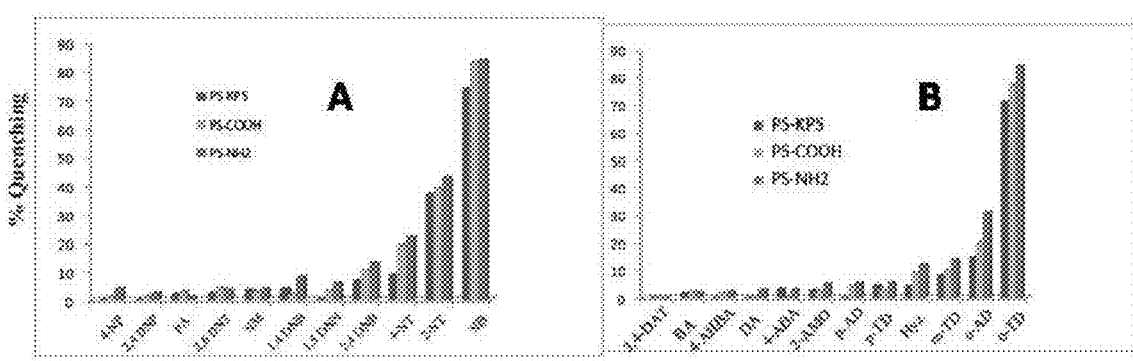
FIG. 2: Comparative plot of different volatile (A) nitro and (B) amine compounds with PS-KPS, PS—COOH and PS-NH$_2$. Emission is collected at 400 nm ($\lambda$ex=390 nm). The powder strip (as described in experimental section) is exposed to the respective vapours for 15 min.

Solid powders of the polystyrene nanoparticles, in the form of strip prepared as per the aforementioned procedure is exposed to different analyte and the resulting change is monitored via change in the PL spectra. The chemical sensing capability of the fluorophore incorporated polystyrene nanoparticles, different analytes are subjected to exposure from their vapour phase. Subsequent changes measured from their solid state emission showed the ability of the corresponding nanoparticle for sensing the analyte. Analysis of the observed values described different scenarios for various analytes depending on their electronic state; nanoparticles interact effectively with analytes having high electronic deficiency, bringing in their selectivity towards those analyte. Nitrobenzene is found to incur highest quenching from OPV emission and o-toludine for PBI emission. When the polymers are exposed to the saturated vapour of the analyte for 15 min, nitrobenzene (in case of nitro compounds) and o-toulidine (in case of amine compounds) showed the highest quenching efficiency to either of OPV or PBI respectively (FIG. 2). In spite of higher vapour pressure of 2-nitrotoluene it was observed to show less % quenching for OPV when compared to nitrobenzene which possess more electron accepting ability while for o-anisidine with more electron donating ability compared to o-toulidine which possess higher vapour pressure was seen to show less % quenching for PBI.

On contact with vapours of specific electron deficient nitroaromatics; OPV emission got selectively quenched to show yellow emission from the nanobeads under UV radiation. While exposure to amine vapour quashed PBI emission selectively and one observes blue emission under UV lamp. Such a vast range of color alteration from white to either blue or yellow from the same sensor makes it a true dual analyte sensor with two distinct outputs.

Figure 3:
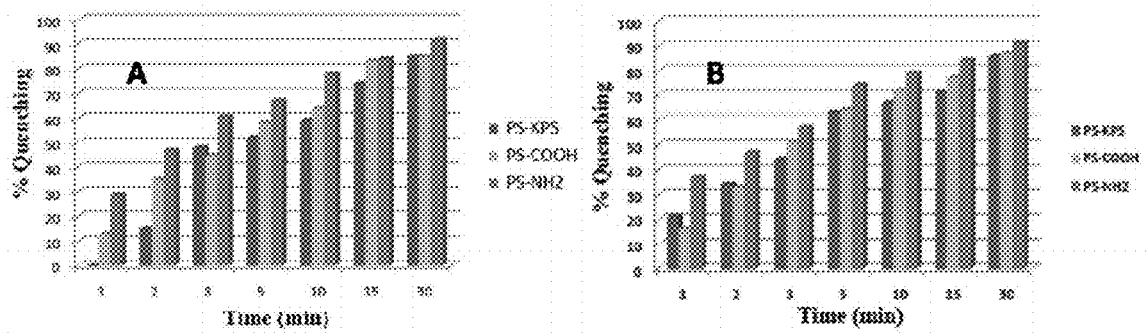
FIG. 3: Comparative plots for percentage (A) OPV and (B) PBI emission quenching for the three nanobeads (PS-NH$_2$, PS—COOH and PS-KPS) upon exposure to nitrobenzene/o-toulidine vapours as a function of time.
Figure 4:
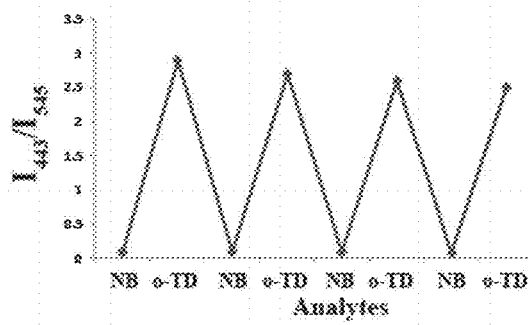
FIG. 4: Multi-analyte detection on dipping the free standing film of PS-NH$_2$ simultaneously onto nitrobenzene and o-toulidine solution in methanol. Emission spectrum is collected every minute after dipping into the respective analyte solution.

Control of surface functionality (—COOH, —NH$_2$ and neutral) on the nanobeads played a pivotal role for boosting the sensing efficiency; introduction of functionality on the surface alleviate analyte-sensor interaction through hydrogen bonding, prompting their fast responsiveness. From the time varied study of luminescence quenching upon analyte interaction, it is observed that the sensing efficiency of the polymers evolved with time. Thus for the case of PS-KPS, time required for 50% quenching of emission intensity through interaction with suitable analyte is more or greater than 2 min for OPV quench, and 2 min for PBI quench). However for the case of functionalized nanoparticles (PS—COOH and PS-NH$_2$) similar quenching is readily observed within 2 min, accounting for almost two fold enhancement in the sensing efficiency. This boosting of the analyte sensing performance is a result from the functionality present on the surface of the nanoparticles (FIG. 3). It is observed that the nanobead with amine functionality (PS-NH$_2$) on the surface shows the highest sensing efficiency than the other two for both electron deficient and rich analytes. Real time, possible for device based application has been demonstrated with free standing film. The fabricated film is capable for efficient detection of fast analyte exchange from diluted solution and it can be reused up to 8 cycles (FIG. 4).

In view of the above, the present invention provides a distinctly dual vapour based solid state emitting sensor having donor and acceptor dyes together into polystyrene nanobeads. The surface of nanobeads was selectively functionalized with amine (PS-NH$_2$), carboxy (PS-COOH) and their sensing efficiency is compared with the one having no functionalization (PS-KPS).

As observed from the digital images of the polymers as chemical sensors, and from the solid state emission, presence of nitrobenzene results in a clear and distinct change of the emission property from white to blue. Similar trend is observed when the subsequent change is monitored through CIE diagram, shifting the co-ordinates from (0.29, 0.31) to (0.43, 0.56) upon exposure with nitrobenzene vapour and to (0.19, 0.16) upon exposure to o-toluidine vapour. These newly obtained co-ordinates lie in the yellow and blue region of the CIE diagram, respectively.

In one embodiment, the present invention provides a kit for the detection of volatile organic compounds (analyte) comprising fluorescent polymer having both perylene bisimide (PBI) and oligo (p-phenylene vinylene) (OPV) fluorophores with carboxy and amine functionality.

In another preferred embodiment, said volatile organic compounds (analyte) is selected from nitrobenzene (NB), 4-nitrotoluene (4-NT), 2,6-dinitrotoluene (2,6-DNT), picric acid (PA), 1,4-dinitrobenzene (1,4-DNB), 2-nitrotoluene (2-NT), 1,3-dinitrobenzene (1,3-DNB), 2,4-dinitrophenol (2,4-DNP), 4-nitrophenol (4-NP), 1,5-dinitronaphtahlene (1,5-DNN), nitromethane (NM), o-toulidene (O-TD), m-toulidine (m-TD), p-toulidine (p-TD), O-anisidine (O-AD), p-anisidine (p-AD), 4-aminobenzoic acid (4-ABA), o-dianisidine (o-DA), 4-amino-3-hydroxy benzoic acid (4-AHBA), 2,6-diaminotoluene (2,6-DAT), hydrazine (Hyz), 2-amino-2-methyl 1-proanol (2-AMP) or n-butylamine.

Figure 5:
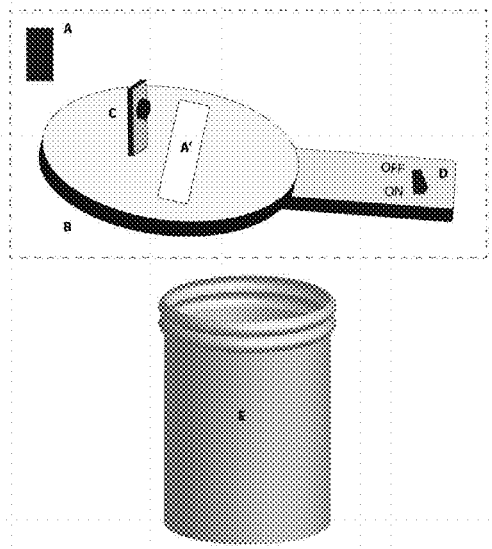
FIG. 5: Kit Diagram

In one embodiment, the kit comprising for detection of volatile organic compounds comprising:
a) a sensor cartridge film (A) prepared by drop casting the polymer in suitable solvent solution followed by drying, or by sticking polymer powder onto an adhesive tape secured on a cardboard frame;
b) a base (B) for the portable kit which contains a cut space (A') for attaching the sensor cartridge film (A);
c) an UV light assembly (C), attached vertically to the base (B) for illuminating the sensor cartridge;
d) The power button (D) for the UV light is located at the handle portion of the base and
e) an analyte chamber (E) that is used to hold the 'to be analyzed' sample. (FIG. 5).

The solvent is selected from the group consisting of THF, DCM or chloroformate.

To check the functionality of the kit, first place and secure the sensor cartridge (A) on the assembly point (A'), with the provided holder clips and then switch on the UV lamp (C) using the power switch (D). If the sensor cartridge film appears as white emitting, the kit is ready to go. To analyze a liquid sample, a portion of the sample is first to be transferred to the analyte chamber (E) and then (i) the sensor cartridge film can be dipped into the sample followed by soaked drying and attaching to the designated place on the base or (ii) covering the chamber with the base (B) containing the sensor cartridge in such a way that the sensor cartridge can be effectively exposed to the vapour generated from the analyte. For the case of gas samples, the kit assembly can be directly exposed in a way similar to method (ii). Once the sensor cartridge is sufficiently exposed (for 30 sec) to the analyte liquid/vapour, the base (B) kit can be taken off from the analyte chamber and the UV lamp (C) be switched ON from the power switch (D). If the sensor cartridge appears as blue under UV illumination, then the analyte contains organic amine. If the sensor cartridge appears as yellow under UV light, this indicates the presence of nitroaromatic compound in the analyte sample.

In one embodiment of the present invention, the polymer can be used in form of powder directly or free standing film can also be casted.

The free standing film is prepared by drop casting THF solution of the polymer and subjected to different analytes (nitrobenzene as most responsive nitroaromatics and o-toluidine as most responsive amine) from their individual methanolic solutions (100 μL in 30 ml MeOH). As observed from its powder form, the film shows identical white emission from the dry state or on exposure to pure methanol. But when the film is dipped in the methanolic solution of nitrobenzene for a minute, the emission changes to yellow similar to that observed from powder from under vapour exposure and the submerging of the film in o-toluidine solution produces dark blue emission, in co relation with previous observation.

It is observed that, when the film used for nitrobenzene detection is directly dipped in o-toluidine solution, it shows exactly similar emission property, and vice versa. However, at any point of time the film can be made to regain its white emission by simply washing with few drops of methanol. The advantage of the film, being able to detect various analytes from a serial analysis, without requirement of any intermediate washing or purification and the observed emission intensity is also comparable with that observed from pristine film. Similar study for up to 8 consecutive cycles of alternating analytes results in no change of the sensing efficiency, thus making the film a highly suitable candidate for application in device fabricate and detect the subjected analyte in less than a minute.

Figure 6:
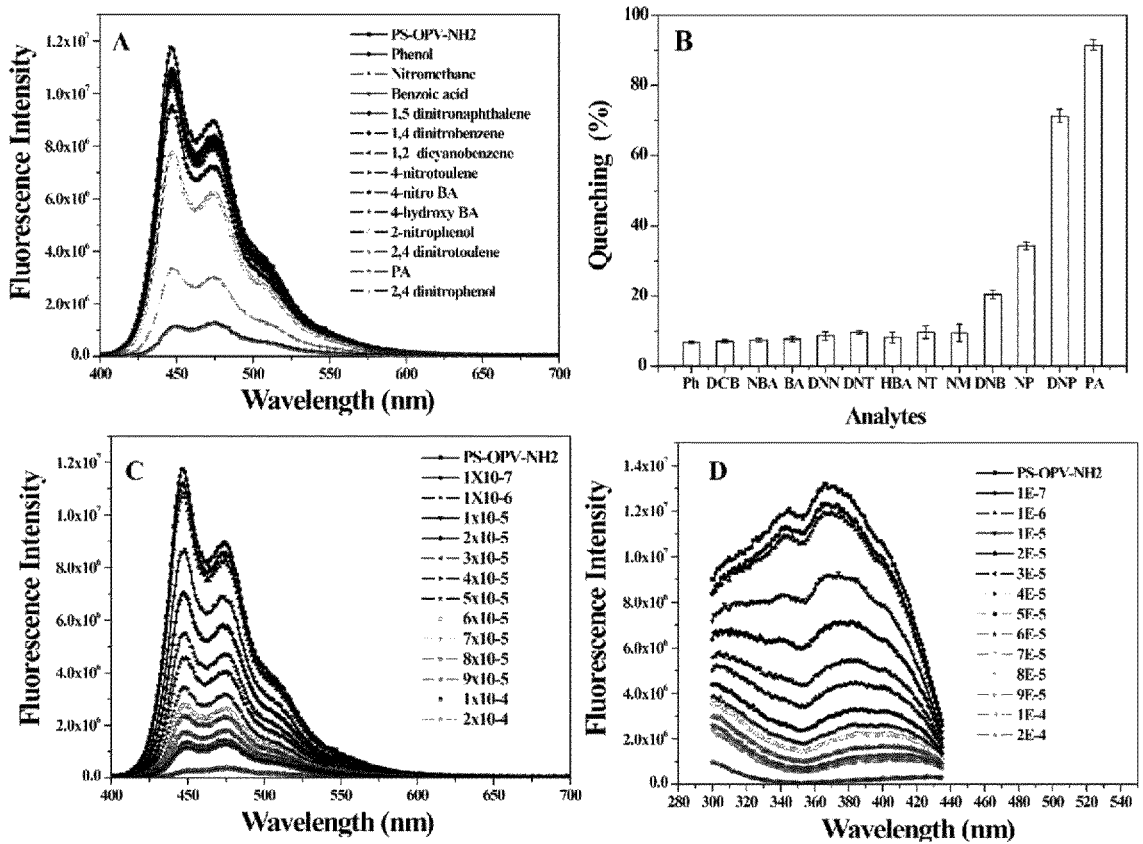
FIG. 6: A) Emission spectra of PS—OPV—NH$_2$ and B) its quenching percentage upon addition of different nitroorganic compounds ($1\times10^{-4}$ M) in water. Error bar indicates standard deviations of three measurements. C) Emission and D) excitation spectra of PS—OPV-NH$_2$ polymer collected after the addition of varying concentration of PA ($1\times10^{-7}$ to $2\times10^{-4}$ M). Emission and excitation spectra is collected at $\lambda$ex=390 nm and $\lambda$em=445 nm respectively.

FIG. 6 depicts A) Emission spectra of PS—OPV-NH$_2$ and B) its quenching percentage upon addition of different nitro-organic compounds (1×10$^{-4}$ M) in water. Error bar indicates standard deviations of three measurements. C) Emission and D) excitation spectra of PS—OPV-NH$_2$ polymer collected after the addition of varying concentration of PA (1×10$^{-7}$ to 2×10$^{-4}$ M). Emission and excitation spectra is collected at λex=390 nm and λem=445 nm respectively.

The linear fitting of plot displayed two clear linear range of I$_0$/I vs PA concentration which ranged from 0 to 30 μM (R$^2$=0.982) and 40 to 70 μM (R$^2$=0.998). The limit of detection is calculated based on signal to noise ratio of 3 and it is estimated to be 58 nM which indicated appreciably high sensitivity of sensor toward PA.

Figure 7:
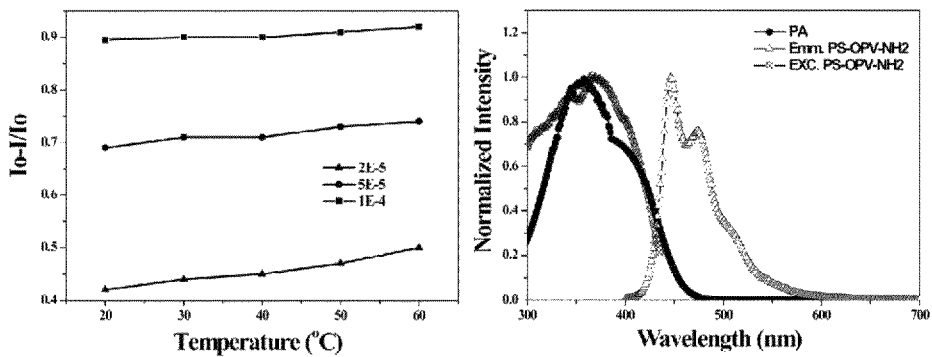
FIG. 7: A) Temperature dependent quenching of polymer emission after PA addition. B) Spectral overlap of excitation/emission spectra of PS—OPV-NH$_2$ with that of absorption spectra of PA.

The absorption spectra of polymer with varying concentration of PA is recorded and no obvious shift or appearance of new peak in the absorption spectra is observed in presence of PA. Evident spectral overlap between emission spectra of polymer and absorption spectra of nitrophenols while inefficient overlap is observed for the rest of the analytes. This result supported the involvement of long range energy transfer in the quenching process. Also, emission quenching efficiency of PA recorded at different temperature confirmed the nature of quenching to be static type. FIG. 7A showed no appreciable change in quenching of polymer after PA addition (2E-5 to 1E-4 M) as a function of temperature (20° C. to 60° C.); confirming static quenching which further verifies energy transfer from polymer to PA. Complete overlap of the absorption spectra of PA ((λ$_{max}$=360 nm) with excitation spectra of polymer ((λ$_{max}$=365 nm) also indicated possibility of inner filter effect which reduces the fluorescence intensity of fluorophore due to competitive absorption by PA resulting in non-linearity between concentration of analyte and observed fluorescence intensity of fluorophore (FIG. 7B). Spectral overlap between emission/excitation spectra of polymer to that of absorption spectra of PA or 2,4-DNP is almost same (FIG. 7B), however % quenching by these compounds followed the order: PA>2,4-DNP>2-NP. This can be attributed to PET via acid base interaction since they all contained one hydroxyl (—OH) group with varying nitro group that governed their acidity. To further verify the role of functional group in sensing, effect of compounds with only —OH group (Ph, 4-HBA) or only —NO$_2$ group (1,4-NBA, 4-NT, 2,4-DNT, 1,2-DCB, 1,5-DNN) on % quenching of polymer is checked. As shown in FIGS. 6 (A and B) no obvious effect on the emission spectra of polymer is observed by their addition which reassured the requirement of both —OH as well as —NO$_2$ group in the sensing mechanism.

It is clear that outstanding selectivity and sensitivity of polymer toward PA sensing in water is due to the combined effect of three mechanisms namely, energy transfer, PET and IFE.

As sensing studies is performed in aqueous medium, it is extremely crucial to check for possible interference from cations and anions that might be present in the contaminated water sample. Almost 16 different cations were chosen including both hard and soft metal ions and as shown in FIG. 8A, B none of the metal ions exhibited any obvious quenching of the emission spectra of PS—OPV-NH$_2$ unlike other sensors where hard metal ions have to be first complexed with EDTA before carrying out PA sensing. This clearly establishes an advantage in terms of ready to use nature of the sensor, without requirement for metal removal through complexation.

Figure 8:
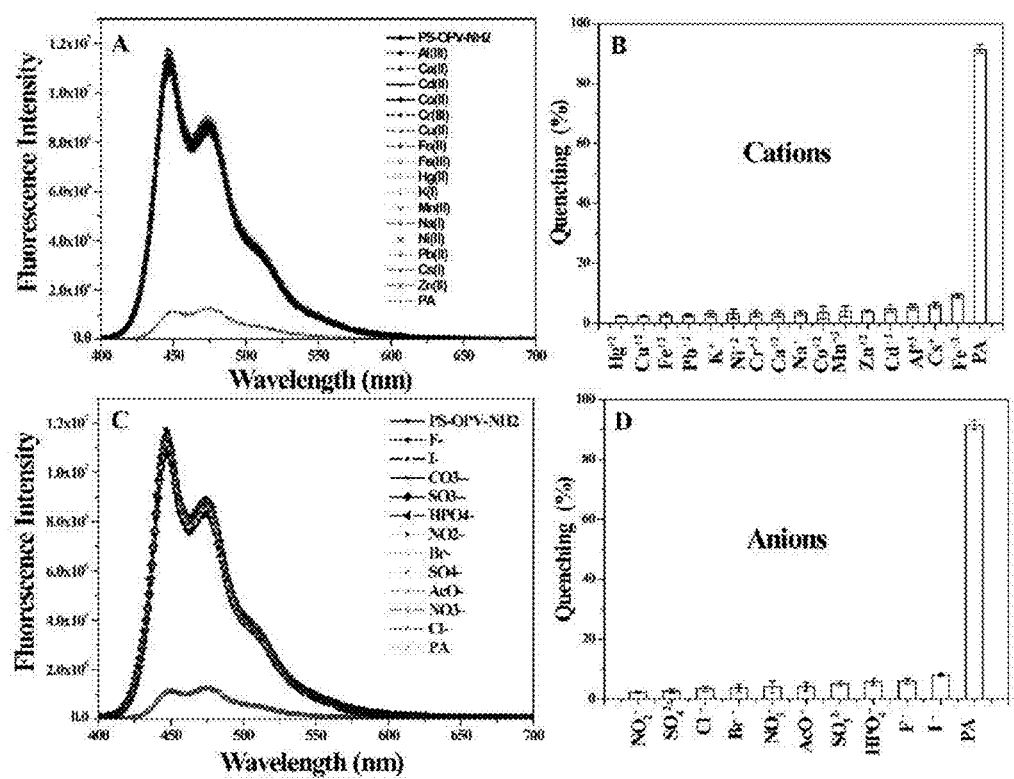
FIG. 8: A) Emission spectra of PS—OPV-NH$_2$. B) its comparative quenching percentage upon addition of different cations vs PA ($1\times10^{-4}$ M) in water. C) Emission spectra of PS—OPV-NH$_2$ and D) its comparative quenching percentage upon addition of different anions vs PA ($1\times10^{-4}$ M) in water. Error bar indicates standard deviations of three measurements.

FIG. 8 depicts A) Emission spectra of PS—OPV-NH$_2$. B) its comparative quenching percentage upon addition of different cations vs PA (1×10$^{-4}$ M) in water. C) Emission spectra of PS—OPV-NH$_2$ and D) its comparative quenching percentage upon addition of different anions vs PA (1×10$^{-4}$ M) in water. Error bar indicates standard deviations of three measurements.

Similarly a library of anions are also checked (FIG. 8C, D) and none are found to affect the emission intensity of polymer. Further explored effect of ionic strength on the sensing efficiency of PA. To demonstrate the same the emission spectra of polymer before and after the addition of 1M NaCl is collected and no change in its emission intensity is observed. Also fluorescence quenching efficiency of PA remained similar even after the addition of 1M NaCl indicating that sensor had the capability to withstand the complex environment and could be used for PA sensing even in sea water.

Scope of PS—OPV—NH$_2$ for real time device based application is tested using a free-standing membrane ($\lambda_{max}$=477 nm), prepared from evaporating the THF solution of the polymer on a glass surface. When the film is dipped in PA contaminated water (PA conc. of 2×10$^{-4}$ M) for 1 min, an instant drop in the emission is observed, measuring 53% quenching of the original intensity. This demonstrated the high potential of OPV—PS-NH$_2$ towards device based application for detection of PA from aqueous medium, in the form of self-standing film.

EXAMPLES

Following examples are given by way of illustration therefore should not be construed to limit the scope of the invention.

The instrumentation used for characterization of the polymers like the GPC, NMR, TEM, UV, DLS, Zeta Potential, Sonicator, TGA and fluorescence spectrophotometer are same as described in (*ACS Biomater. Sci. Eng.* 2017, 3, 1788-1798). The polymer powders were mixed with KBr to make pellets and their infrared spectra was recorded using Bruker α-T spectrophotometer in the range of 4000-600 cm$^{-1}$. The Solid State Quantum yield was carried out using F-3029 Quants-Phi 6" Integrating Sphere connected to Horiba JobinYvon Fluorolog 3 spectrophotometer. Particle size from dynamic light scattering (DLS) was measured thrice to check for consistency. The zeta potential of all the polymers were measured using 1 mM KCl as background electrolyte at pH=7. For solid state photoluminescence, both excitation and emission data were recorded in S1c/R1 mode and slit width was kept at 1 nm throughout the experiments. The Percent Solid content of the latex was determined using the following equation:—

$$SC(\%) = \frac{W_d}{W_l} \times 100$$

where Wd and Wl are the weight of dried polymer and weight of polymer latex respectively. The values for the same are given in table 1.

The pH dependent studies were carried out using 100 μg of polymer that was taken in various mentioned pH (3 mL) followed by recording its emission spectra. For temperature dependent studies, 100 μg of the polymer in 3 mL deionized water was taken and emission spectra was recorded using Peltier sample compartment with a thermoelectric temperature controller and autotone PID. The temperature was set manually with a tolerance range of 0.5° C. and an equilibration time of 10 minute before each reading. The temperature was fixed. All the emission experiments were performed in deionized water and slit width of 1 nm and "S1c/R1" mode was maintained throughout the studies. For TEM, polymer sample in water was drop casted into carbon coated copper grid and solvent was allowed to dry at room temperature.

Example 1: Preparation of Sample for Sensing Studies

For carrying out the vapour sensing analysis, the polymer powders were directly exposed to the analyte vapour. In one such process, transparent adhesive tape was secured on a thin cardboard frame as a support and then polymer powder was adhered on it. This sample strip was then exposed to the analyte vapour and PL measurement was performed to check for its sensing property. For the other case, a free standing film was prepared from THF solution containing 20 mg of polymer per ml of solvent. The solution was poured into a petridish and the solvent was allowed to evaporate at room temperature. The film was then peeled off, cut into desired size and used directly for sensing studies in the similar way. For PA sensing in water nanoparticle dispersion was directly used after purification.

Example 2: Study of the Chemical Sensing

For studying the polymers towards sensing of the analytes from vapour phase, saturated vapour chambers were prepared by placing analytes inside a closed 50 ml centrifuge tube for 24 hours at room temperature (25° C.). After 24 hrs, powder samples in the form of prepared stripes described above was placed inside the centrifuge tube, avoiding any direct contact of the analyte with the sample and the chamber was closed. The sample was then removed from the vapour chamber after the mentioned residence time and emission spectra were recorded immediately. For sensing studies with free standing film, the prepared film was directly dipped into methanolic solution of the analyte (100 µL in 30 ml MeOH) for 1 min and then removed to soak off the excess liquid from the film surface. The emission spectra were recorded with the dried film, without any further delay.

For checking the emission from the OPV moiety of the polymers, the samples were excited at $\lambda_{excitation}$=390 nm and the emission spectra were collected in the range of 400 to 700 nm. While, for PBI, emission spectra was recorded in the range of 500 to 700 nm using $\lambda_{excitation}$=490 nm. The percentage quenching was calculated using following equation (1):—

$$\% \text{ Quenching} = \frac{I_0 - I}{I_0} \times 100 \quad \text{eq 1}$$

$$\frac{I_0}{I} = K[Q] + 1 \quad \text{eq 2}$$

Where $I_0$ and I is initial and final emission intensity at their respective emission maxima before and after the exposure to the analyte.

For sensing studies of nitro-organics in water, 100 µg of PS—OPV-NH$_2$ was dispersed into 3 mL of deionized water. And to the same is added fixed concentration ($10^{-4}$ M) of various analytes like nitromethane, 1,4-Hydroxybenzoic acid, 4-Nitrotoluene, 1,2-Dicyanobenzene, Benzoic acid, 1,5-dinitronaphthalene, 2,4-dinitrotoluene, 1,4-nitrobenzoic acid, 1,4-dinitrobenzene, 2,4-dinitrophenol, 2-nitrophenol, phenol and picric acid. The solution is then subjected to thorough mixing followed by immediate recording of the emission spectra. All the experiments are repeated thrice to avoid any discrepancy and average of the three values is plotted as bar graph along with their standard error. Interference from various anions and cations in water is checked using same concentration ($10^{-4}$ M) for each of the analytes. For free standing film, similar procedure mentioned above is followed. The polymer sample is excited at $\lambda_{excitation}$=390 nm (OPV) and subsequently its emission spectra is collected in the range of 400-700 nm.

Fluorophore grafted polystyrene nanobeads were synthesized through the miniemulsion pathway, where the non-functionalized nanoparticle (PS-KPS) was prepared according to the (*ACS Biomater. Sci. Eng.;* 2017, 3, 1788-1798). Functionalization of such nanoparticles during miniemuslion polymerization was carried out following a modified report from Landfester et al. (*Macromol. Chem. Phys.* 2005, 206, 2440-2449).

Example 3: Preparation of Fluorescent Polystyrene Nanoparticles

In a typical miniemulsion synthetic protocol, organic phase (Styrene (4 gm), OPV and PBI based fluorescent cross-linkers and hexadecane (48 mg)) of the reaction mixture were added dropwise into the aqueous phase (surfactant (12 mg), initiator (16 mg) and respective functional monomers such as acrylic acid or aminoethyl methacrylate hydrochloride (100 mg)) under stirring. This mixture was then allowed to stir at room temperature for another hour for pre-emulsification followed by sonication for 20 min in an ice cooled bath. The polymerization process was carried out for 20 h at 70° C. by stirring at speed of 750 rpm. The detailed reactant amount and reaction condition for both functionalized and non-functionalized nanoparticles. The obtained latex from this step was dialysed, dried and washed several times with methanol to remove excess surfactant, oligomers and unreacted monomers. While in case of PA sensing amine functionalized OPV incorporated nanobeads were synthesized to make OPV—PS-NH$_2$ using the above mentioned protocol. The solid content value of PS—OPV-NH$_2$ is given in Table 2.

Example 4: Estimation for Encapsulation of Dyes into Nanoparticles

For calculating Dye Loading Content (DLC) and Dye Encapsulation Efficiency (DLE) of the polymers, THF solutions having 1 mg/ml concentration of the polymer were taken and their absorbances were recorded at individual absorption maxima (395 nm for OPV and at 520 nm for PBI dye). Based on their molar extinction coefficients (PBITEG, 81092 Lmol$^{-1}$ cm$^{-1}$; OPV, 40360 Lmol$^{-1}$ cm$^{-1}$) the amount of dye incorporated into the polymer has been calculated and subsequently their DLC and DLE has been estimated.

Example 5: Study of Picric Acid Sensing in Water

A. Preparation of Fluorescent Polystyrene Nanoparticles

Amine functionalized OPV incorporated polystyrene nanobeads was prepared as per the reported article. For the same, the organic phase containing 1 gm of styrene, 30 mg OPV and 48 mg of hexadecane was dropwise added to an aqueous phase (4 mL) containing 100 mg of AEMH, 16 mg of ACVA and 33 mg of Brij S-100. This mixture was then pre-emulsified for an hour at room temperature. The obtained emulsion was then sonicated for another 20 min under an ice-cooled bath. Finally, the polymerization was carried out at 70° C. for 20 h with a constant stirring at 750 rpm. The obtained latex was dialyzed using a dialysis membrane (molecular weight cutoff=6 kD) against deionised water for 3 days, with changing water every six hours. The percentage solid content of the polymer was calculated using standard equation.

Advantages of the Invention

1. The present invention provides a dual distinct sensor. When come in contact through vapour with nitroaromatics it becomes yellow under UV lamp while when come in contact with amines becomes blue under UV light.
2. The control of surface functionality (—COOH, —NH$_2$ and neutral) on the nanobeads played a pivotal role for boosting the sensing efficiency; introduction of functionality on the surface alleviate analyte-sensor interaction through hydrogen bonding, prompting their fast responsiveness
3. The kit of the present invention is capable of efficient vapour (powder) as well as solution (Free standing film) sensing.
4. Visual color change which can be detected under UV lamp.
5. The film of the present invention is reusable film up to 8 cycles.
6. Fast exchange of the analyte is possible.
7. Detection in no time (1 min in case of free standing film).

The invention claimed is:

1. A dual distinct sensor including a polymer comprising:
   a fluorophore perylene bisimide (PBI); and
   an oligo (p-phenylene vinylene) (OPV) functionalized with carboxy and amine functional groups and a polystyrene (PS) backbone,
   wherein the dual distinct sensor detects analytes in visual solid and liquid states, and
   wherein the dual distinct sensor gives a distinct emission when coming in contact with vapours of either amines or nitroaromatics.

2. The dual distinct sensor as claimed in claim 1, wherein said analytes are selected from the group consisting of nitrobenzene (NB), 4-nitrotoluene (4-NT), 2,6-dinitrotoluene (2,6-DNT), picric acid (PA), 1,4-dinitrobenzene (1,4-DNB), 2-nitrotoluene (2-NT), 1,3-dinitrobenzene (1,3-DNB), 2,4-dinitrophenol (2,4-DNP), 4-nitrophenol (4-NP), 1,5-dinitronaphtahlene (1,5-DNN), nitromethane (NM), o-toulidene (O-TD), m-toulidine (m-TD), p-toulidine (p-TD), O-anisidine (O-AD), p-anisidine (p-AD), 4-aminobenzoic acid (4-ABA), o-dianisidine (o-DA), 4-amino-3-hydroxy benzoic acid (4-AHBA), 2,6-diaminotoluene (2,6-DAT), hydrazine (Hyz), 2-amino-2-methyl 1-propanol (2-AMP) and n-butylamine.

3. The dual distinct sensor as claimed in claim 1, wherein said polymer possesses high molecular weight in the range of 114600 to 157600 with polydispersity index varied from 2.3 to 3.1.

4. The dual distinct sensor as claimed in claim 1, wherein said polymer is used in powder form or film form.

5. A process for detection of analytes using a dual distinct sensor including a polymer comprising:
   a fluorophore perylene bisimide (PBI); and
   an oligo (p-phenylene vinylene) (OPV) functionalized with carboxy and amine functionality groups and a polystyrene (PS) backbone,
   the process for detection of the analytes comprising the steps of:
   a) securing transparent adhesive tape on a thin cardboard frame as a support followed by adhering polymer powder on said tape to obtain a sample strip;
   b) exposing said sample strip to a vapour of the analytes and performing photoluminescence measurement to check for sensing property;
   c) preparing a saturated vapour chambers by placing the analytes inside a closed centrifuge tube for 24 to 30 hours at a temperature in a range of 25° C. to 30° C.
   d) placing the sample strips inside the centrifuge tube, avoiding any direct contact of the analytes with the sample strip, and closing the vapour chamber; and
   e) removing the sample strip from the vapour chamber and recording an emission spectra,
      wherein the dual distinct sensor detects the analytes in visual solid and liquid states, and
      wherein the dual distinct sensor gives a distinct emission when coming in contact with vapours of either amines or nitroaromatics.

* * * * *